United States Patent [19]
Daikuzono

[11] Patent Number: 5,623,940
[45] Date of Patent: Apr. 29, 1997

[54] CATHETER APPARATUS WITH A SENSOR

[75] Inventor: Norio Daikuzono, Chiba-ken, Japan

[73] Assignee: S.L.T. Japan Co., Ltd., Tokyo, Japan

[21] Appl. No.: 284,963

[22] Filed: Aug. 2, 1994

[51] Int. Cl.$^6$ .................................................. A61B 5/00
[52] U.S. Cl. ........................ 128/736; 128/639; 606/15
[58] Field of Search ............... 606/2, 3–18; 128/736, 128/642, 639; 604/117

[56] References Cited

U.S. PATENT DOCUMENTS

| | | | |
|---|---|---|---|
| 4,512,762 | 4/1985 | Spears . | |
| 4,913,142 | 4/1990 | Kittrell et al. | 606/7 |
| 5,084,043 | 1/1992 | Hertzmann et al. | 606/3 |
| 5,222,953 | 6/1993 | Dowlatshahi | 606/15 |
| 5,292,309 | 3/1994 | Van Tassel et al. | 604/117 |
| 5,425,355 | 6/1995 | Kulick | 606/13 |

FOREIGN PATENT DOCUMENTS

WO90/13333  11/1990  WIPO .

Primary Examiner—David M. Shay
Attorney, Agent, or Firm—Lowe, Price, LeBlanc & Becker

[57] ABSTRACT

A catheter apparatus has an information detecting sensor which is capable of positively controlling an intended treatment effect at a selected position at which laser energy is irradiated, to treat conditions such as solidification or necrosis of tissue. The catheter apparatus comprises a rigid sheath formed to be safely inserted into a body cavity. A window is provided at the front end portion of the sheath to allow a movable sensor to be moved in or out through the window. A balloon means having an inflatable balloon is provided in the sheath adjacent to the sensor. The balloon means is secured to the sheath and is biased through an opening on the opposite side of the sheath toward an adjacent wall portion of the body cavity in a direction opposite to the side of the window when the balloon is inflated. The sensor is thereby projected through the window and is brought into close contact with a correspondingly adjacent portion of the cavity wall by a reaction force of the inflated balloon.

7 Claims, 16 Drawing Sheets

DISTANCE FROM WALLS OF THE URETHRA

CATHETER APPARATUS WITH A SENSOR

DETAILED DESCRIPTION OF THE INVENTION

1. Field of the Invention

The present invention relates to a catheter apparatus having a sensor which is inserted into a body cavity such as the esophagus, stomach, rectum for detecting information on or transmitting therethrough the wall of the cavity. In particular, the present invention relates to a catheter apparatus having a sensor which is inserted into the rectum for detecting the temperature of the wall of the rectum in combination with a laser balloon catheter which is inserted into the urethra for conducting the laser treatment for the prostata.

2. Background of the Related Art

Laser balloon catheters are used for opening the clogged vessel or are used for hyperthermia treatment for cancer tissue by irradiating it with laser light.

The structure of this type of laser balloon catheter is disclosed in U.S. Pat. No. 4,512,762. In this patent, a lumen tube is provided so that it surrounds an optical fiber. The lumen tube is provided at the front end thereof with a balloon which surrounds the front end of the optical fiber.

Another structure is disclosed PCT International Publication W090/13333. A probe comprises a shaft and a sleeve. The shaft is provided with an ultrasonic sensor at the front end thereof. A window is formed in the wall of the front end portion of the shaft. The front end portion of the laser fiber which passes through the shaft is located in the window. The probe is surrounded at the front end thereof by the balloon and at the base end thereof by an outer cylindrical casing. The balloon is inflated by supplying a space between the outer cylindrical casing and the sleeve with, for example, water for biasing the wall of the urethra. Under this biasing condition, the prostata is irradiated with laser light from the front end portion of the laser fiber.

Although irradiation position of laser light is detected on a real time basis from a position within the urethra with an ultrasonic sensor while the prostata is irradiated with laser light in the PCT Int. Pub. W090/13333, the degree of solidification or necrosis of the prostata where it is irradiated with laser light can not be detected.

SUMMARY OF THE INVENTION

Therefore, it is a principal object of the present invention to provide a catheter apparatus having an information detecting sensor which is capable of positively controlling the treatment effect of the position where laser is irradiated, for example, the degree of the solidification or the necrosis in the laser light irradiation treatment for prostata and the like.

In order to accomplish the object, in a first aspect of the

In a preferred embodiment of the invention, there is provided a catheter apparatus having a sensor which is inserted into a body cavity for detecting information at the wall of the body cavity or transmitted therethrough. It includes a rigid sheath which is to be inserted into said body cavity. A window is opened at a front end portion of the sheath and a sensor is provided which is movable in or out through said window. A balloon means is a provided an inflatable balloon which is adjacent to the sensor. The balloon means is secured inside the sheath and is biassed toward the wall of said body cavity in a direction opposite to the side of the window when the balloon is inflated, said sensor thereby being projected through the window and brought into pressure contact with the adjacent wall by the reaction force of the balloon.

In each aspect, a sensor may be chosen which is adapted to detect at least one of a temperature of the tissue, a quantity of laser light and a level of ultrasonic energy transmitted to the tissue being treated.

The balloon means may comprise a probe and a balloon mounted thereon. The balloon may be inserted into the sheath together with the probe. The probe may be secured to and within the sheath.

The probe has a hollow body which is closed at its front end and is formed with a communication hole on the wall of the front end portion thereof. The balloon is provided in such a manner that it surrounds the communication hole. The balloon is inflated by fluid pressure supplied through the communication hole via the inside of the hollow body.

The probe may have a larger length than that of the sheath and is removably disposed with the sheath. The probe is secured to the sheath at the front end and base end sides with respect to the window.

The sheath may be formed on the outer surface thereof with graduations which are spaced in a longitudinal direction of the sheath for indicating the degree of insertion of the sheath.

The sheath may be provided on the outer surface thereof with a stop having the shape of collar. Said stop is movable in a longitudinal direction of the sheath. The stop may be provided with means for securing the stop to the sheath.

In the treatment of the prostata, the laser balloon catheter is inserted into the urethra and the prostata is irradiated with laser light to heat the prostata for promoting solidification or necrosis. Clinical resulta show that burden on the patient is less, cure is fast and curing effect is high.

Since the prostata is located in a position about 5 to 15 mm deeper from the inner wall of the urethra in the prostata laser treatment, it is necessary to comparatively increase the power of laser light for heating the prostata to a given temperature. However, irradiation with laser light of excessive high power density will cause the tissue in the vicinity of the wall of the urethra to be excessively heated. This results in damage of the tissue in the vicinity of the urethra and difficulty in treatment as well as thermal damage to the rectum.

Therefore, it is necessary to control the power of the incident laser light to prevent the tissue in the vicinity of the urethra from being damaged to enhance the curing effect and to prevent the rectum from being thermally damaged. The present inventors have found that it is an effective approach for the treatment of the prostata that a probe having a thermal sensor at the front end thereof is inserted into the rectum for detecting the temperature of the wall of the rectum and its temperature signal is fed back to a laser light output control apparatus to control the power of laser light incident to the prostata or the power density for preventing thermal damage to the prostata or the rectum.

Even if the temperature of the wall of the rectum is desired to detect by inserting, for example, the probe having a thermal sensor having a front end thereof, it is difficult to constantly bring the thermal sensor into close contact with the thermal sensor. If the sensor is not in close contact therewith, accurate wall temperature detection is difficult. Appropriate feed-back control can not be effected.

In accordance with the present invention, there is provided a catheter apparatus having a sensor which is inserted into a body cavity for detecting information on the wall of the body cavity or transmitted therethrough, comprising a holder having a rigidity; a sensor secured to the holder on one side of the front end portion thereof; and a balloon means having a balloon secured to the holder, which is inflated on the opposite side of the sensor, whereby when said balloon is inflated with fluid pressure supplied into the balloon of said inflating means, the balloon is biased upon the wall of the body cavity, the holder being adapted to be biased in a direction far away from the balloon so that said sensor is brought into pressure contact with said wall.

Accordingly, the sensor is positively brought into close contact with the wall of a body cavity such as rectum by inflation of the balloon so that accurate temperature of the wall of the rectum can be detected. As a result, the energy of laser light incident upon the prostata can be appropriately controlled. This prevents damage to the tissue in the vicinity of the urethra, enhances the curing effect and prevents the thermal damage to the rectum.

In the first aspect, the sensor is secured or integral with the holder. Accordingly, the holder will deviate toward the sensor when the balloon is inflated. In contrast to this, in the second aspect, a catheter apparatus having a sensor comprises a sheath having a rigidity which is to be inserted into said body cavity; a window which is opened at the front end portion of the sheath; a sensor which is movable in or out through said window, and a balloon means having an inflatable balloon which is adjacent to the sensor. The balloon means is secured to the sheath and is biassed on the wall of said body cavity in a direction opposite to the side of said window when said balloon is inflated. The sensor is projected through the window and is brought into pressure contact with said wall by the reaction force of the balloon. That is, the sensor is movable into or out from the sheath through the window of the sheath by the inflation of the balloon.

In each aspect of the invention, the sensor which is capable of detecting at least one of the tissue temperature, the quantity of laser light transmitting through the tissue and the level of the ultrasonic energy can be adopted. As mentioned above, detection of the tissue temperature is important to primarily prevent the damage to the rectum. For the treatment of the prostata, the catheter apparatus of the present invention is provided with a sensor for detecting the quantity of incident laser light, such as photodiode or phototransistor. The quantity of laser light which is absorbed by the prostata and the quantity of laser light reaching the rectum can be determined by detecting the quantity of light which is emitted from the laser balloon catheter inserted into the urethra and transmitted through the prostata to the rectum. An ultrasonic wave sensor may be used. The ultrasonic wave sensor is capable of detecting the position of the prostata by impinging the ultrasonic wave upon the prostata. Damage to the sphincter due to insertion to a wrong position can be prevented by determining the insertion position of the laser balloon catheter into the urethra based upon a signal representing the position of the prostata. A plurality of thermal sensors or photodiodes are provided in a longitudinal direction of the catheter apparatus of the present invention. When any one of the signals from the plurality of sensors exceeds a preset signal level, control is made to lower the output of the laser light.

The balloon means may comprise a probe and a balloon mounted thereon. The balloon may be inserted into the sheath together with the probe. The probe may be secured to and within the sheath. The probe has a hollow body which is closed at the front end thereof and is formed with a communication hole on the wall of the front end portion thereof. The balloon is provided in such a manner that it surrounds the communication hole. The balloon is inflated by fluid pressure supplied through the communication hole via the inside of the hollow body. The balloon can be inflated by pumping, for example, air through a probe and is deflated due to its recovery force by purging the air. The probe may have a larger length than that of the sheath and be removably disposed with the sheath. The probe may be secured to the sheath at the front end and base end sides with respect to the window. It is effective that the balloon means be separate from the sheath, since the balloon is made of, for example, rubber latex, if the balloon is deteriorated, the new balloon can be inserted into the sheath together with the probe after only deteriorated balloon is replaced with new one.

The sheath may be formed on the outer surface thereof with graduations which are spaced in a longitudinal direction of the sheath for indicating the degree of insertion of the sheath. The sheath is provided on the outer surface thereof with a stop having the shape of collar. Said stop is movable in a longitudinal direction of the sheath. The stop is provided with means for securing the stop to the sheath. The degree of insertion into the rectum can be adjusted by forming on the outer surface of the sheath graduations representative of the insertion degree of the sheath. The insertion position can be maintained by fixing the stop to the sheath while the sheath is inserted into an optimum position.

The sensor may have a sensor holder and sensor terminals. The sensor holder may be formed on the outer surface with a plurality of protuberances. The sensor terminals may be located on the protuberances. The sensor terminals can be positively brought into contact with the inner wall of the body cavity such as the rectum by arranging the sensor terminals and the protuberances so that they project with respect to the sensor holder.

DETAILED DESCRIPTION OF THE PREFERRED EMBODIMENTS

The present invention will become more clear from the following description of the preferred embodiments with reference to the drawings. The catheter apparatus of the present invention is inserted into the rectum for control of the output of laser light when another laser balloon catheter apparatus is inserted into the urethra to irradiate the prostata with laser light for treatment therefor.

Now, an embodiment of the laser balloon catheter will be described with reference to FIGS. 1 to 4.

Figure 1:
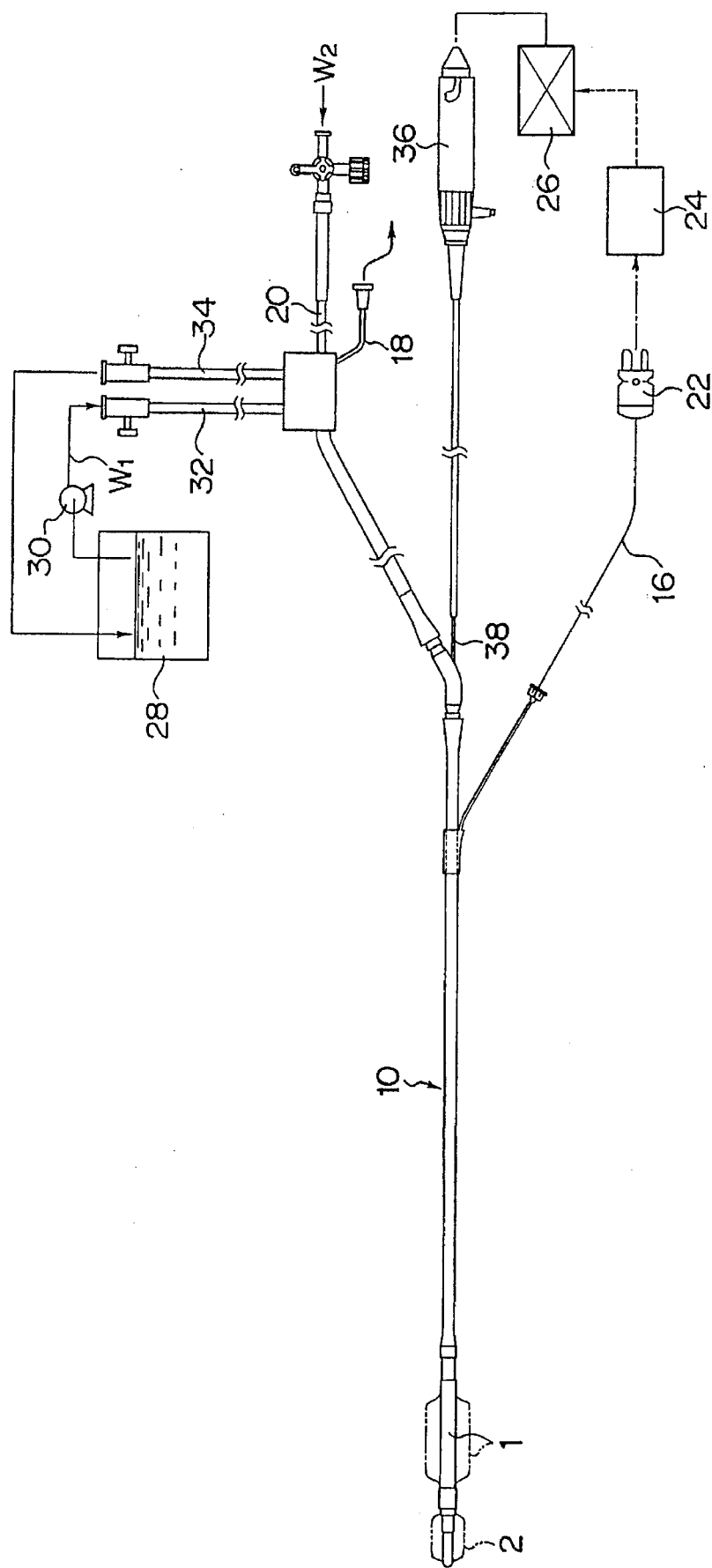
FIG. 1 is a view of the whole of a laser balloon catheter apparatus which is inserted into the urethra.

FIG. 1 shows the whole of the laser balloon catheter which is provided with a first and second balloons 1 and 2 at the front end of the insertion guide 10. The insertion guide 10 has an inner first guide 12 and second guide 14 which surrounds the same. A lead 16 for a thermal sensor, a urine discharge conduit 18 and a tube 20 for supplying coolant to inflate the second balloon are provided between the first and second guides 12 and 14. The lead 16 for the thermal sensor is connected to a connector 22 so that a signal is input to a temperature control unit 24 via the connector 22 for driving a laser light generator 26. Urine which is discharged during treatment will be discharged via the urine discharge conduit 18. The second balloon inflation coolant supply tube 20 is supplied with, for example, water W2.

On the other hand, fluid such as water W1 for inflating the first balloon 1 is supplied from a coolant tank 28 via a conduit 32 by a circulating pump 30 and then passes through a space between the first and second guides 12 and 14 for inflating the first balloon 1. Thereafter, it reaches the first guide 12 and passes through the first guide 12 and is returned to coolant tank 28 via the discharge tube 34. The coolant tank 28 is adjusted to a given temperature.

Laser light, preferably Nd-YAG laser light from the laser light generator 26 is transmitted through an optical fiber 38 via the connector 36.

Figure 2:
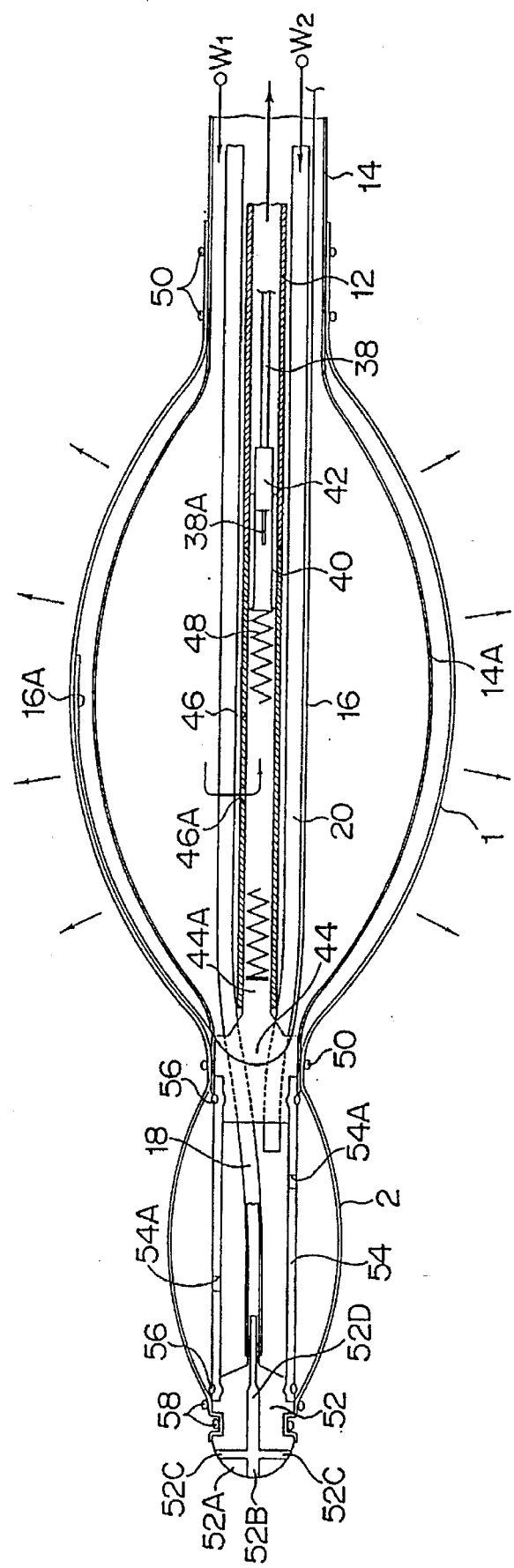
FIG. 2 is a longitudinal sectional view showing the structure of the front end portion of the laser balloon catheter.

Structure of laser balloon catherter at the front portion thereof is illustrated in detail in FIG. 2. The optical fiber 38 is provided in the first guide 12 made of plastics such as polyethylene. A protection tube 40 having a high rigidity and resistance to heat is provided within the front end portion of the first guide 12. A holder 42 of a metal is disposed within the protection tube 40 to hold the front end of the optical fiber 38.

Figure 3:
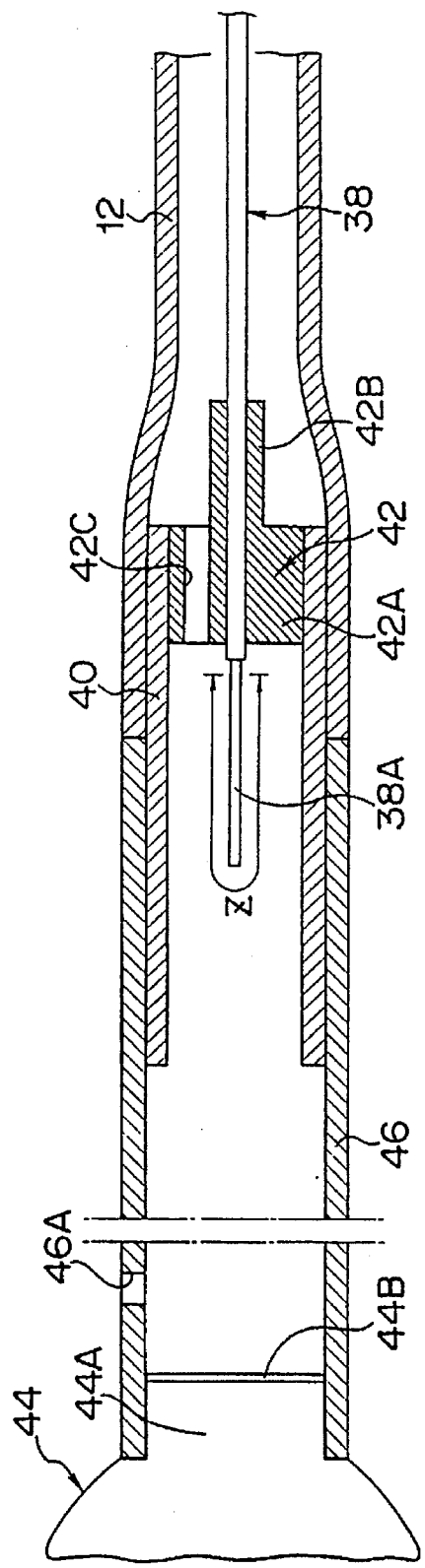
FIG. 3 is an enlarged longitudinal sectional view showing the main portion of the catheter.
Figure 4:
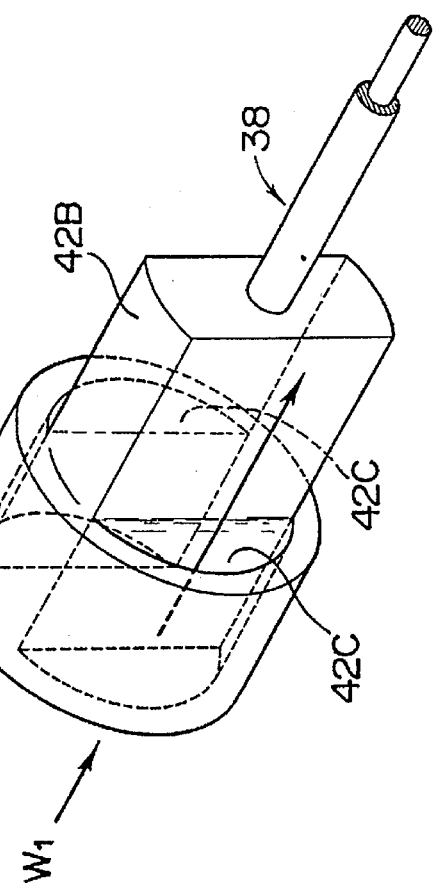
FIG. 4 is a perspective view of a holder.

Manner of holding of the optical fiber 28 is illustrated in FIGS. 3 and 4. The holder 42 has a circular portion 42A and a flat holding portion 42B on the front and rear end sides thereof, respectively. The circular portion 42 is formed with throughholes 42C on the both sides thereof. The holder 42 is plated with a reflective metal, such as gold for reflecting the laser light. The optical fiber 38 passes through the holding portion 42B and the circular portion 42A and is not covered with any cladding on the front portion extending beyond the front end of the circular portion 42A so that a core 38A is exposed. Accordingly, laser light is emitted from the core portion 38A. In this case, much laser light is emitted from the front end of the core 38A than from the other area due to its linear transmission characteristics. In order to cause more laser light to be emitted from the side of the core, the core is roughed and coated at the area represented at a reference Z in FIG. 3 with a coating including a light scattering material and light absorbing powders such as carbon powders for converting light energy into thermal energy.

A connector 44 serving as connecting means is provided at a laser light emitting end, that is, in front of the front end of the optical fiber. The connector 44 has a reduced diameter portion 44A at the rear end thereof. A first link tube 41 made of plastic material through which laser light is transmittable is provided as first link means between the reduced diameter portion 44A and the protection tube 40 and it surrounds the periphery of both of the reduced diameter portion 44A and the protection tube 40. The first tank tube 46 is abutted to the front end of the first guide 12 on the outer surface of the protection tube 40. The first link tube 46 is formed with a communicating hole 46 at an appropriate position. A coil spring 48 is provided within the first link tube 46 between the rear end of the reduced diameter portion 44A and the front end of the protection tube 40. The coil spring is coated with a laser light reflective coating such as gold plating on the outer surface thereof. The reduced diameter portion 44A is formed with a laser light reflective coating such as gold plating 44B on the rear end face thereof.

Laser light is preferably scattered on the inner surface of the first link tube 46 and the protection tube 40. Scattering may be achieved by roughing the inner surface of the first link tube 46 and the protection tube 40 and/or depositing powers of alumina or silica by baking.

The second guide 14 is made of a flexible plastics such as ethylene acetate resin, or polyethylene and has an inflated portion 14A which is preliminarily inflated in the front end portion thereof. The front end of the second guide 14 covers the periphery of the connector 44 and is fastened thereto together with the first balloon 1 by being bound with a fastening means such as strings 50.

A shoe 52 made of a metal, for example is provided in front of the connector 44. The shoe 52 is linked with the connector 44 through a second connecting tube 54 made of a flexible plastics which forms the second linking means. The second link tube 54 is fastened to the shoes 52 and the connector 44 at the opposite ends thereof by being bound with string 56. The second link tube 54 is formed with communicating hole 54A.

In the embodiment, the tube which constitutes the first balloon 1 extends forward through the connector 44 to the shoes 52 to form a second balloon 2. The tube which forms the first balloon 1 is linked to the second guide 2 by being bound with strings 51. In another embodiment, the first balloon 1 is separated from the second balloon 2. The second balloon 2 is bound at the front end thereof with fastening means such as strings 58 so that it is fastened to the shoe 52. The first and second balloons 1 and 2 are made of a material having a flexibility and elasticity and is inflatable. In the embodiment, latex rubber is used. Silicone rubber may also be used.

The shoe 52 has a semispherical portion 52A, a cylindrical portion and a diameter reduced portion at the front, intermidiate and rear portion thereof, respectively. The shoe 52 is formed with a main urine discharge opening 52B and subsidiary urine opening 52C which open at the center and both sides of the semispherical portion 52A. The urine discharge inlets are communicated with a common urine discharge passage 52 which opens at the rear end of the diameter reduced portion.

The urine discharge conduit 18 is fitted to the diameter reduced portion of the shoe 52. The urine discharge conduit 18 extends through the connector 44 and then the first guide 14 and opens externally as shown in FIG. 1. Accordingly, if urination occurs during operation, urine flows into any of the urine discharge openings and is discharged via the urine discharge passage 52D and conduit 18. Provision of the urine discharge means is very effective since urination desire is promoted by the warming of the prostata on operation thereof. The purpose of the urine openings which are provided at the central front end and the opposite sides is to smoothly intake the urine via the opening if any of the other openings are clogged with the bladder wall.

On the other hand, the second balloon inflating coolant supply tube 20 extends within the first guide 14 and through the connector 44 and terminates within the second link tube 54. Externally supplied cooling water W2 passes through the second balloon inflating coolant supply tube 20 and the second link tube 54, the communicating hole 54A and is then introduced into the second balloon 2 to inflate the second balloon 2. The second balloon 2 is deflated by purging the cooling water W2 through the second balloon inflating coolant supply tube 20.

The lead 16 for the thermal sensor extends between the first and second guide 12 and 14 and is turned along the outer periphery of the connector 44 and extends through the second guide 14 and is in contact with the inner wall of the first balloon in the intermediate thereof along the length thereof as shown in FIG. 2. The front end of the lead 16 is sandwiched between two reflective strips 16A made of aluminum foil or plastic sheets containing white pigment. The reflective strips 16A are bonded to the inner wall of the first balloon 1.

The laser balloon catherter having such a structure may be preferably used for the treatment of the prostata. If the cooling water W1 and W2 is not pumped in pressure, the first and second balloons 1 and 2 are deflated due to its deflating characteristics. At this time, the second guide 14 due to deflection of the first balloon.

Figure 5:
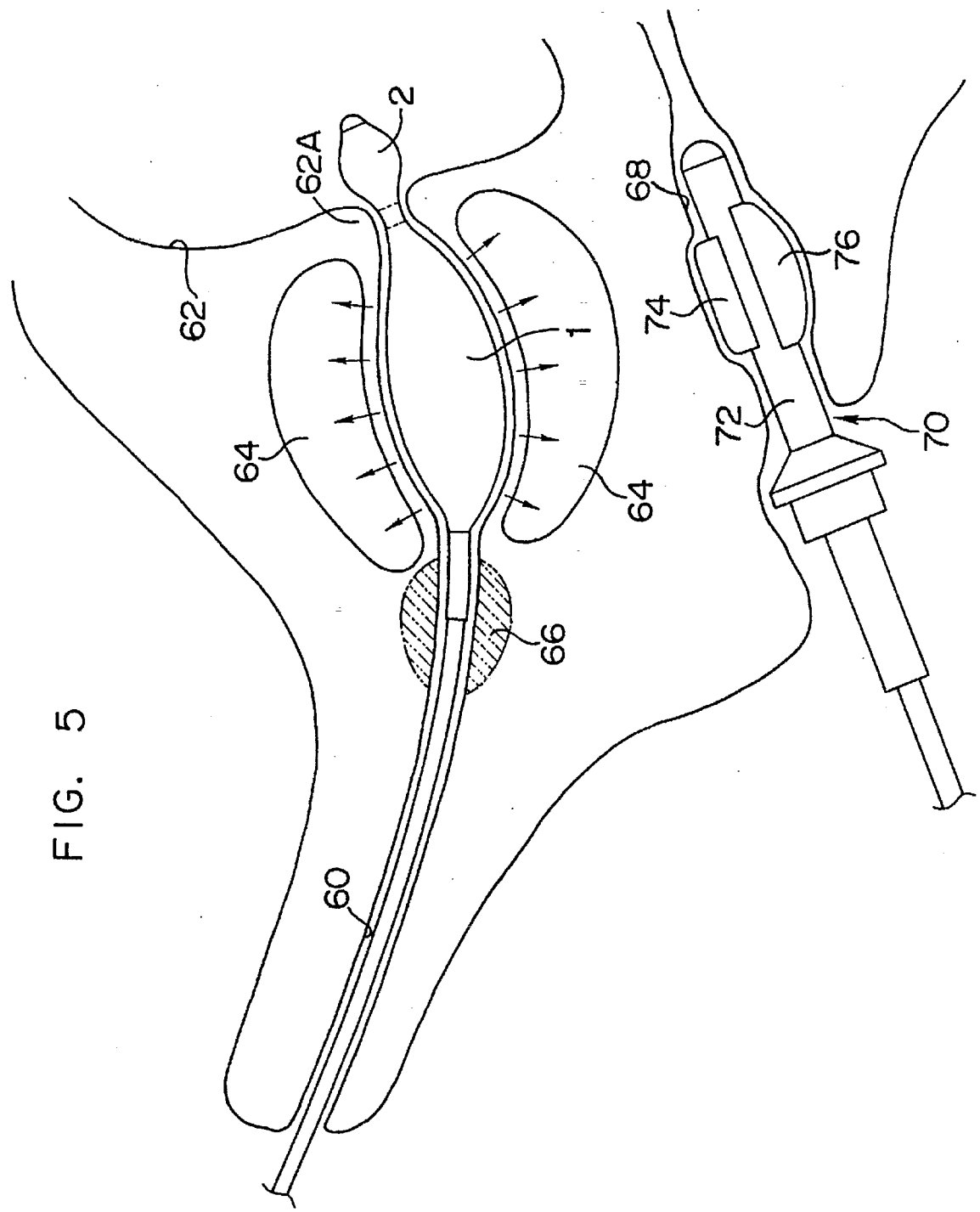
FIG. 5 is an explanatory view showing the treatment of the prostata and the detection of the temperature in the rectum.

Under this condition, the laser balloon catheter is inserted into the urethra 60 so that the second balloon 2 is located within the bladder 62 as shown in FIG. 5. Subsequently, the cooling water W1 is supplied from the water tank 28 via the conduit 32 by the circulating pump 30 and is introduced into the inflation portion 14A of the second guide 14 through a space between the first guide 12 and the second guide 14 for inflating the inflation portion 14A. This inflation causes the first balloon 1 also to be inflated as shown in FIGS. 2 and 5. The cooling water W1 used for inflation flows into the first guide 12 via the communicating hole 46 and flows into the first guide 12 and then is returned to the cooling water tank 28 via the discharge tube 34.

The cooling water W2 is also supplied into the second link tube 54 through the second balloon inflating coolant supply tube 20 and is introduced to the second balloon through the communicating hole 54A for inflating the second balloon 2 as shown in FIGS. 2 and 5.

Under this condition, laser light is incident upon the optical fiber 38 from the laser light generator 26 via the connector 36 and is emitted from the core 38A which is located at the front end of the fiber. Among the emitted laser light, the laser light which is impinged upon the protection tube 4 or the first linking tube 46 is transmitted therethrough or is reflected on the inner surface of the tube 40 or 46 and is finally diffused laterally and is transmitted through the second guide 14 and the first balloon 1 and is incident upon the prostata. The laser light having linearly transmitting component is reflected on the gold plated coil spring 48 when it collides therewith during linearly transmission thereof and is diffused laterally and is incident upon the prostata 64 via the first link tube 46, the second guide 14 and the first balloon 1. Laser light which has linearly transmitted without colliding with the coil spring 48 is reflected on the gold plating film 44B. A part of the reflected laser light is diffused laterally when collides with the coil spring 48 while it travels rearwardly. Rearwardly linearly travelling light is reflected on the gold plated front face of the circular portion 42A of the holder 42 so that it will travel forwardly again. While the laser light is repeatedly reflected on the gold plated film 44 in the rear of the connector 44 and the gold plated front face of the circular portion 42A, it will be laterally diffused. Therefore, laser light is incident upon the prostata from the entire surface of the first balloon 1 in such a manner that the quantity of emitted light is higher and lower at the intermediate and opposite end portions of the balloon 1, respectively.

The laser light which is incident upon the prostata is absorbed by the tissue of the prostata 64 and is converted into heat. As a result of this, the prostata 64 is warmed or heated. Heating by the laser light is maintained for a given period of time. The tissue in the prostata 64 is irradiated with laser light so that it is warmed or heated. The warmed or heated tissue will be solidified or necroses so that it will be prematurely recovered after operation. If laser light, particularly Nd-YAG laser is used, it will be absorbed in the protein in the tissue.

Although heating of the prostata with ultrasonic waves may be possible, most of the ultrasonic waves will be absorbed in the water content in the tissue of the prostata, resulting in heat generation. Energy from ultrasonic waves is less readily absorbed in the tissue than is laser energy, hence the curative effect is lower. In contrast to this, laser light, particularly Nd-YAG laser light is absorbed by water content at a ratio of about 10% and the rest will be absorbed by the protein in the tissue. Therefore, the corresponding curing effect is higher.

In the above mentioned embodiment, cooling water W1 is circulated through a space between the first and second guides 12 and 14 and is then introduced into the first guide 12 via the communicating hole 46 and is discharged via a space in the first guide 12. Alternatively counter flow may be possible.

In the above mentioned embodiment, the first link tube 46 is provided separately from the first guide 12 for facilitating assembly of the apparatus. In assembly, the holder 42 and the protection tube 40 should be provided at the front end of the first guide 20 and the spring 48 should be disposed within the first linking tube 46. Accordingly, the first linking tube 46 may be omitted and the first guide 12 may be extended so that it is adapted into the diameter reduced portion 44A. In this case, the first guide 12 is formed with a communication hole for cooling water W1.

Although Nd-YAG laser light is optimal as laser light, other laser light such as Argon laser light or diode laser light may be used. Since such laser light is less absorbed by water, It will be transmitted through cooling water if it is used. The tissue can be irradiated with enough laser light. Usable laser light includes KTP laser light, dye laser light, KTP/Nd-YAG combined beam laser light.

In the above mentioned embodiment, the fluid for inflating the first and second balloon 1 and 2 is cooling water. It may be gas, such as air, nitrogen gas, carbon oxide gas or other cooling liquid such as alcohol.

Figure 6:
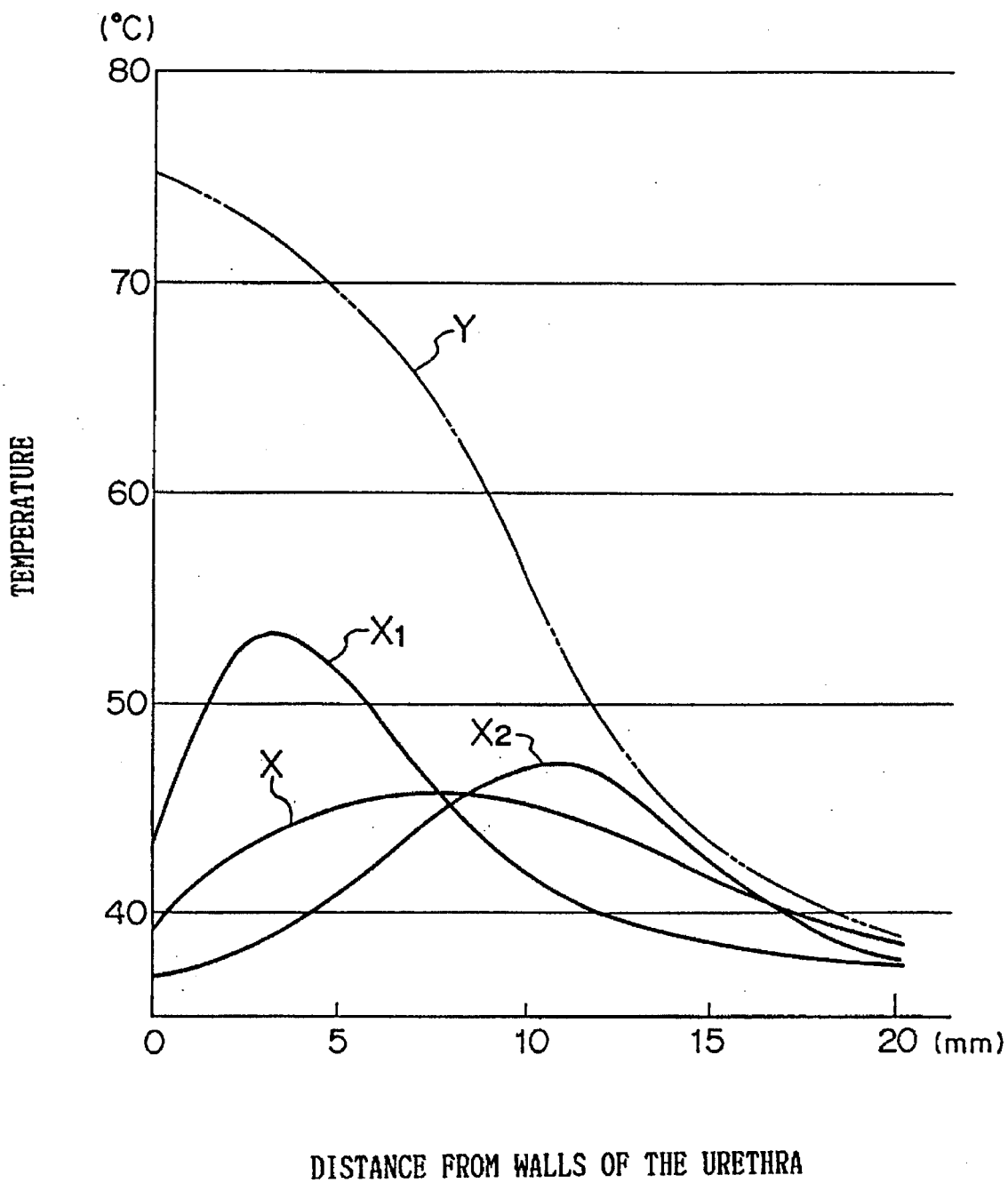
FIG. 6 is an exemplary view showing temperature distributions in a depth direction from the inner wall of the urethra when forced cooling is done and is not done.

In order to smoothly insert the laser balloon catheter of the embodiment into the tissue, it is preferable that the first and second guides 12 and 14 and the first and second link tubes 16 and 54 be flexible. If it suffices to insert in a rectlinear manner, at least one of these components may be non-flexible. On the other hand, in the embodiment the inside of the first balloon 1 is cooled by the cooling water W1 forcedly circulating through the second guide 14 so that it is maintained at a given temperature. If the forced cooling is not accomplished, the power of the laser light becomes lower as the light travels from the inner wall of the urethra to the deep area of the prostata. As shown in FIG. 6 of the temperature distribution curve Y, the tissue which is closer to the inner wall of the urethra is heated to higher temperature and the deeper portion of the prostata is at lower temperature.

If the power of the laser light is increased in order to heat the central portion of the prostata (about 6 to 12 mm deep from the inner wall of the urethra), the portion in the vicinity of the urethra is excessively heated so that the tissue in the vicinity of the urethra is damaged, resulting in difficulty in curing.

If the first balloon and the inflation portion 14A of the second guide 14 are supplied with cooling water W1 for cooling, the tissue in the vicinity of the urethra is cooled as shown in the temperature distribution curve of FIG. 6 so that the tissue is prevented from being damaged while enough laser light is incident to the central portion of the prostata so that the central portion thereof may be positively heated. In this case, the temperature distribution can be adjusted as shown in temperature distribution curve X1 or X2 of FIG. 6 by controlling the power of the laser light and the circulation amount and temperature with cooling water. Curing effect can be enhanced by adjusting the temperature distribution depending upon the symptom of the prostata.

For prostatitis and the like, the inside of the prostata is heated at low temperature not higher than 43° C. while forcedly cooled with cooling water W1. For the treatment of prostatomegaly, forced cooling with cooling water W1 is conducted with water W to protect the inner wall of the urethra or the tissue in the vicinity thereof from being thermally damaged while the inside of the prostata is heated above 45° C. for solidification or necrosis. The solidified or necrosed tissue will be metabolically absorbed so that the prostata is reduced and urethra is opened.

The length of the balloon 1 and the deflation portion 14A of the second guide 14 or the position of the front end of the optical fiber 38 is preset in such a manner that the laser light is not incident to the sphincter portion 66.

The second balloon 2 is effective primarily to position the laser balloon catherter and secondarily to prevent the laser balloon catherter from being removed from the bladder 62. The laser balloon catherter is inserted until the second balloon 2 is located in the bladder 62 as shown in FIG. 5. Thereafter, the second balloon 2 is inflated and then the laser balloon catherter is removed until it abuts on the neck portion 62A of the bladder 62. This causes the first balloon 1 to be preset to a position corresponding to the prostata 64. After completion of presetting, the first balloon 1 is inflated. Even if the laser balloon catherter is displaced during operation, removal of the laser balloon catherter from the bladder 62 is prevented since the second balloon 2 will abut upon the neck portion 62A of the bladder 62A.

The temperature of the inner wall of the urethra is detected by a thermocouple provided at the front end of the lead 16. A signal representative of the temperature is inputted to a temperature control unit 24 via the lead 16 and a connector 22. The temperature of the inner wall of the urethra is controlled by adjusting the turn-on or off time of the laser light generator 26 depending upon the deviation between the detected temperature signal and a target inner wall temperature of the urethra. In case where the target temperature is the temperature of the central portion of the prostata, control of the temperature of the central portion of the prostata is possible by preliminarily determining the correlation between the temperature of the prostata and that of the inner wall of the urethra.

Since excessive heating of the prostata due to excessive laser light incidence will damage the tissue of the prostata, a catheter apparatus 70 for detecting the temperature is inserted into the rectum 68 as shown in FIG. 5.

The temperature detecting catheter apparatus 70 comprises a thermal sensor 74 including a plurality of, for example, about 5 thermocouples having their front ends thereof locating on one side of the front end portion of an insert 72 made of, for example, a metal having a high rigidity and further comprises a biasing balloon 76 on the other side of the insert 72. The leads of respective thermocouple of the thermal sensor 74 are electrically connected to an external unit such temperature control unit 24. The biasing balloon 76 is inflated by means of an external fluid pressurizing source such as air compressing course after the insert 72 of the temperature detecting catheter apparatus 70 is inserted into the rectum 68. The biasing balloon serves to bias insert 72 toward the prostata for bringing the insert 72 into close contact with the inner wall of the rectum 68.

On exposure of the prostata 64 with laser light, the prostata 64 is warmed or heated and part of the laser light transmits through the prostata 64 toward the rectum 68 for heating also the tissue in the vicinity of the rectum 68. The temperatures on the inner wall of the rectum 68 are detected by a thermal sensor 74. When any of the temperatures exceeds a preset temperature, control is made by extending the turn-off period of the laser light generator 26 or by lowering the power of the laser light by the laser light generator 26 for preventing the prostata 64 from being excessively heated or the rectum 68 from being thermally damaged.

Figure 7:
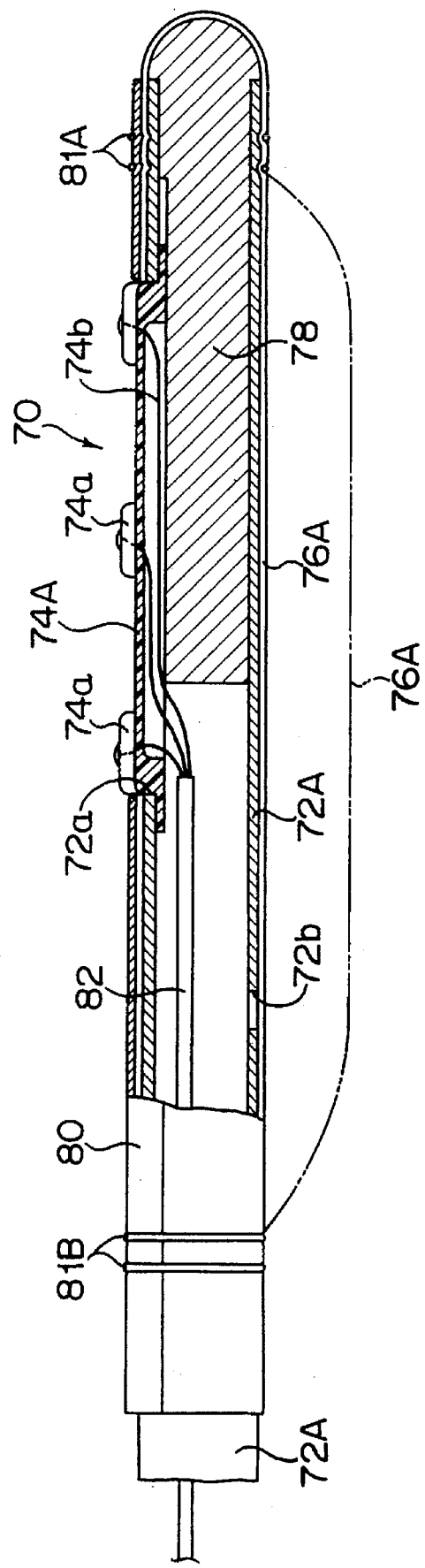
FIG. 7 is a partial sectional outer view of a temperature detecting catheter apparatus in accordance with a first embodiment of the present invention.
Figure 8:
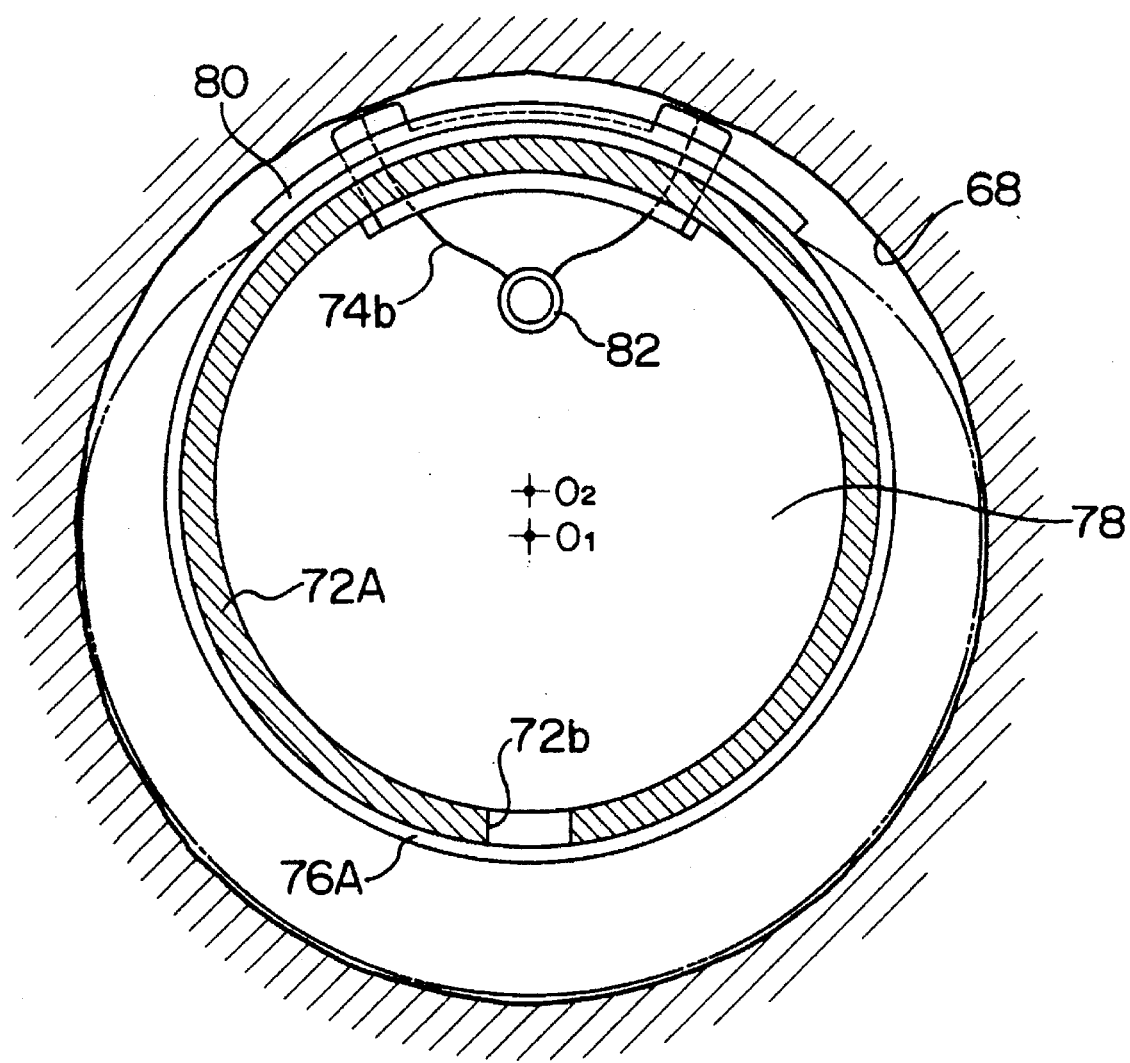
FIG. 8 is a cross sectional view showing the catheter which is inserted into the urethra.

A first embodiment of the temperature detecting catheter apparatus 70 in the present invention is shown in FIGS. 7 and 8.

The holder 72A made of a metallic tube is provided at the front end thereof with a thermal sensor 74A. The holder 72A is formed on one side of the holder 72A with a window 72a into which a thermal sensor 74A is adapted. In order to firmly secure the thermal sensor 74A, a plug 78 made of plastics, for example, is inserted into the front end of the holder 72A so that the outer surface of the plug 78 is in close contact with the inner surface of the thermal sensor 74A and the thermal sensor 74A is in close contact with the inner surface of the holder 72A.

The holder 72A and the plug 78 are covered on their outer surfaces with a biasing balloon 76A made of rubber latex which is in the form of tube having a bottom with a portion corresponding to the window 72a being omitted. As clearly shown in FIG. 8, a restricting plate 80 made of a metal having an arched cross section abuts on the outer surface of the biasing balloon 76A. The restricting plate 80 is made integrally with the biasing balloon 76A with threads 81A and 81B. The portion of the restricting plate 80 corresponding to the above mentioned window 72a is cut away.

On the other hand, the holder 72A is formed with a communicating hole 72b. The holder 72A is communicated with an air supply source (not shown). The biasing balloon 76A excepting the portion which is restricted by the restricting plate 80 is inflated by supply of air as is shown with a phantom line in FIG. 7 and is deflated by discharge of air. The temperature detecting catheter apparatus 70 which is inserted into the rectum 68 along the central axis 01 thereof is displaced to the axis 02 by a biasing force exerted by inflation of the biasing balloon 76A so that the thermal sensor 74A is biased upon the inner wall of the rectum.

The thermal sensor 74A has five protuberances for facilitating the contact with the tissue. A thermocouple is located on the outer surface of each protuberances 74a. The leads 74b are connected at the front ends thereof with the thermocouple and are connected at the base ends thereof with the temperature control unit 24. A reference numeral 82 denotes a protection tube surrounding the leads 74b.

Since the thermal sensor 74A is secured to the holder 72A in the above mentioned temperature detecting catheter apparatus 70, the center axis of the holder 72A is displaced from 01 to 02 due to inflation of the biasing balloon 76A when the inner wall of the rectum 68 serves as a reaction seat.

In this ease, it is necessary to inflate the balloon at a relatively high pressure to displace the holder 72A. Accordingly, a balloon having a strength resistant to the high pressure is required. If the holder 72A is inclined with respect to the center axis of the rectum 68 after the holder 72A is inserted into the rectum 68, the thermal sensor 74A abuts at one end thereof along the longitudinal length thereof upon the inner wall of the rectum 68 and is separated therefrom at the other end thereof. This may make it difficult to accurately detect the temperature over the longitudinal length.

Accordingly, it is preferable that the thermal sensor 74 be displaced as an single body in association with inflation and deflation of the biasing balloon in accordance with the second embodiment of the present invention.

Figure 9:
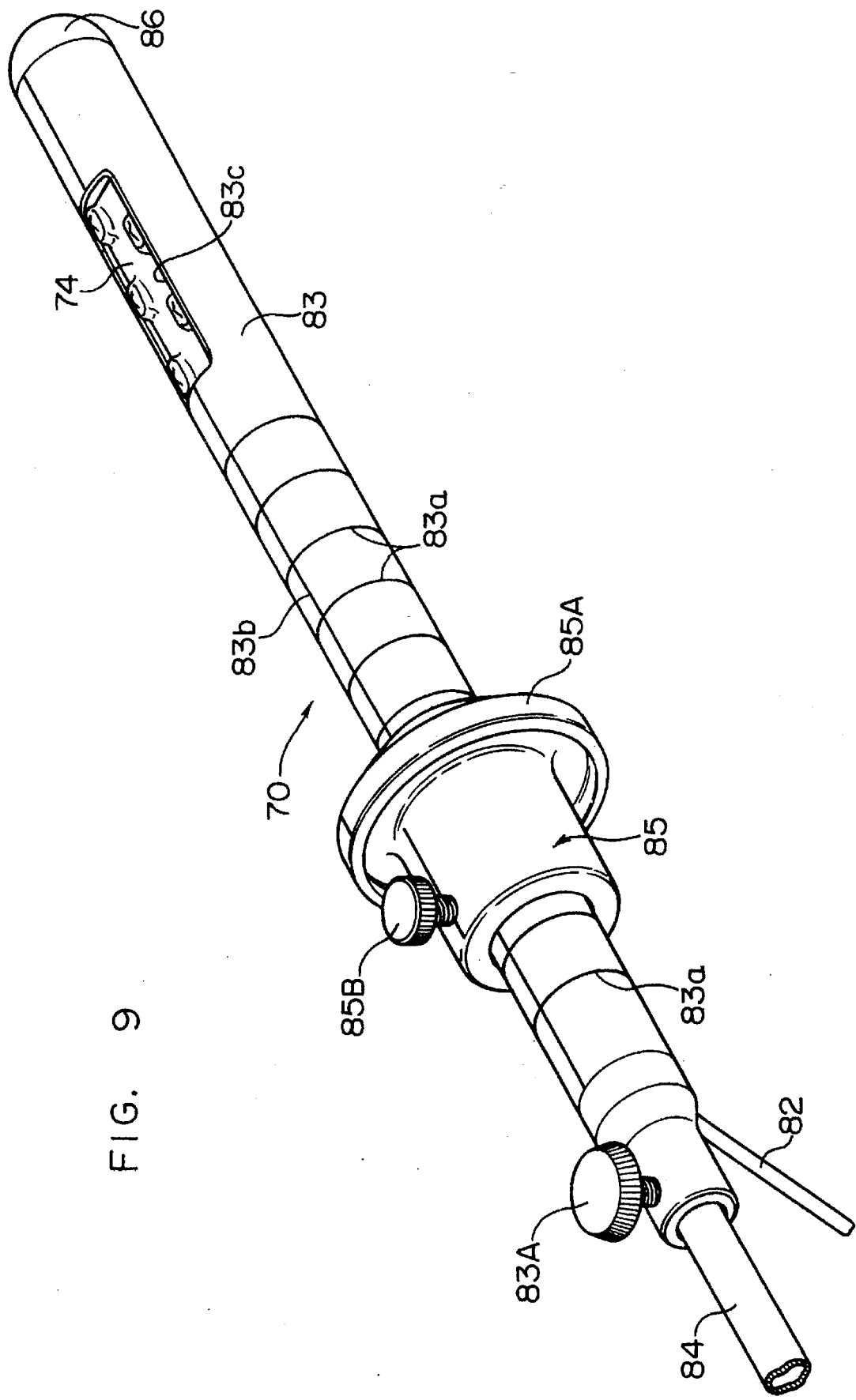
FIG. 9 is a perspective view of the temperature detecting catheter apparatus in accordance of a second embodiment of the present invention.
Figure 13:
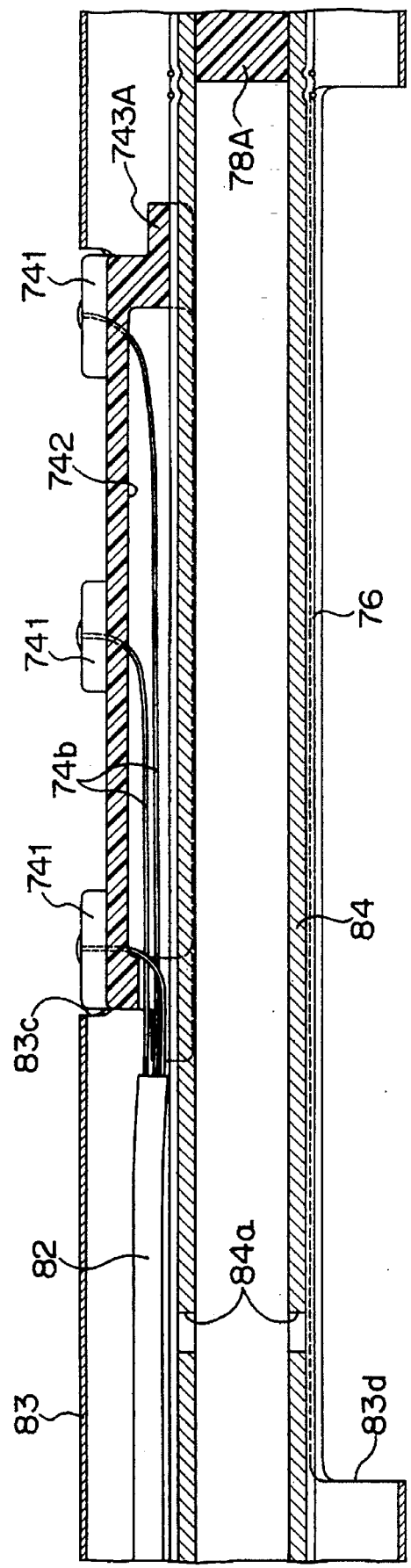
FIG. 13 is an enlarged longitudinal sectional view showing a main part of FIG. 11.
Figure 14:
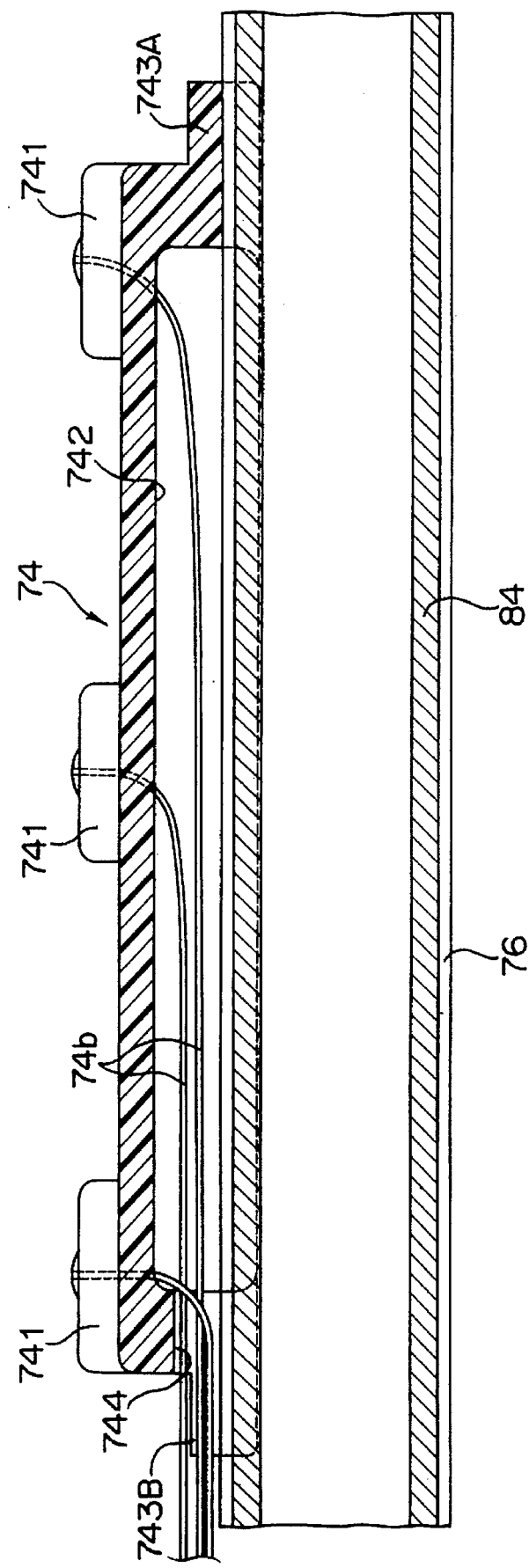
FIG. 14 is an enlarged longitudinal sectional view of a thermal sensor.
Figure 15:
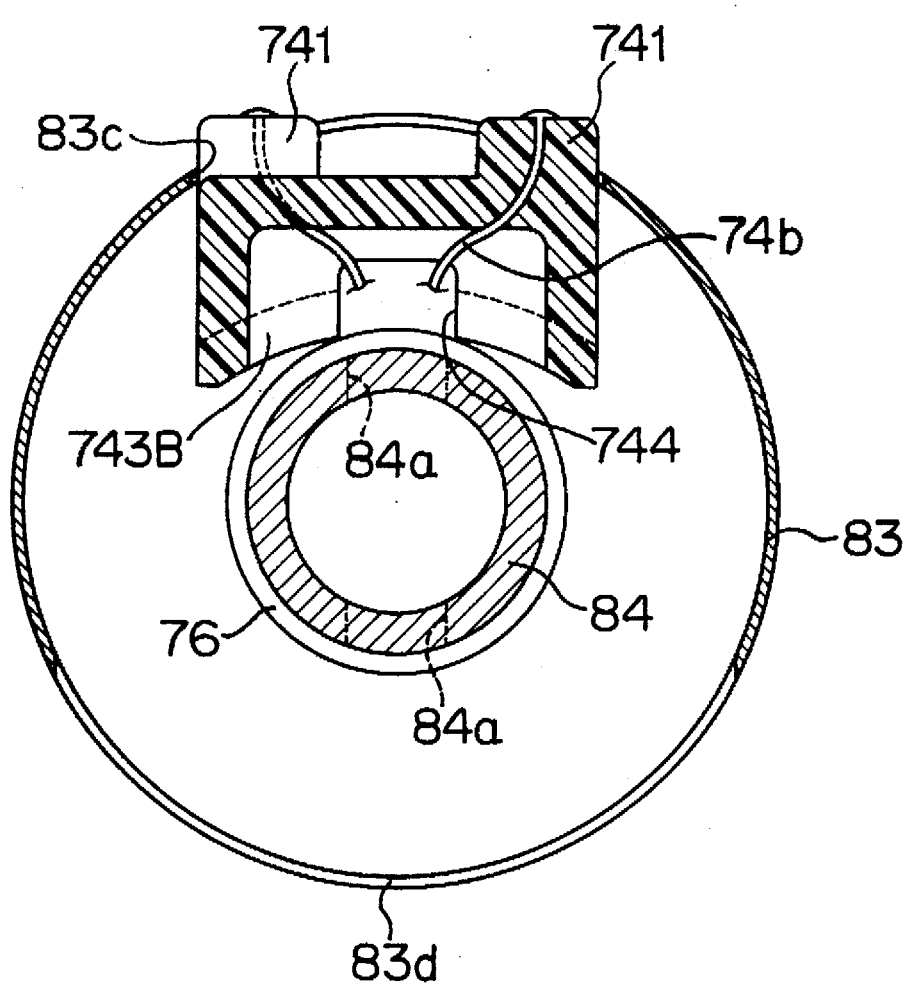
FIG. 15 is a cross sectional view of the temperature detecting catheter apparatus in accordance of the second embodiment of the present invention.

The corresponding second preferred embodiment of the present invention is illustrated in FIGS. 9 through 15. FIGS. 9 and 15 show the whole of the temperature detecting catheter apparatus 70 which comprises a sheath 83, probe 84, thermal sensor 74 and a stop 85. The sheath 83 is made of, for example, stainless steal and is formed on the outer periphery thereof from the middle to the rear area with graduations 83a which are spaced along the length thereof to indicate the degree of insertion of the sheath 83 into the rectum 68. Although the graduations 83a are formed on the sheath 83 from the middle to the rear portion thereof, they may be formed over the entire of the length thereof. A marking 83b which is continuous in a longitudinal length is representative of the center in a peripheral direction of the thermal sensor 74. The thermal sensor 74 can be positioned toward the prostata by aligning the marking 83b with the prostata.

Figure 10:
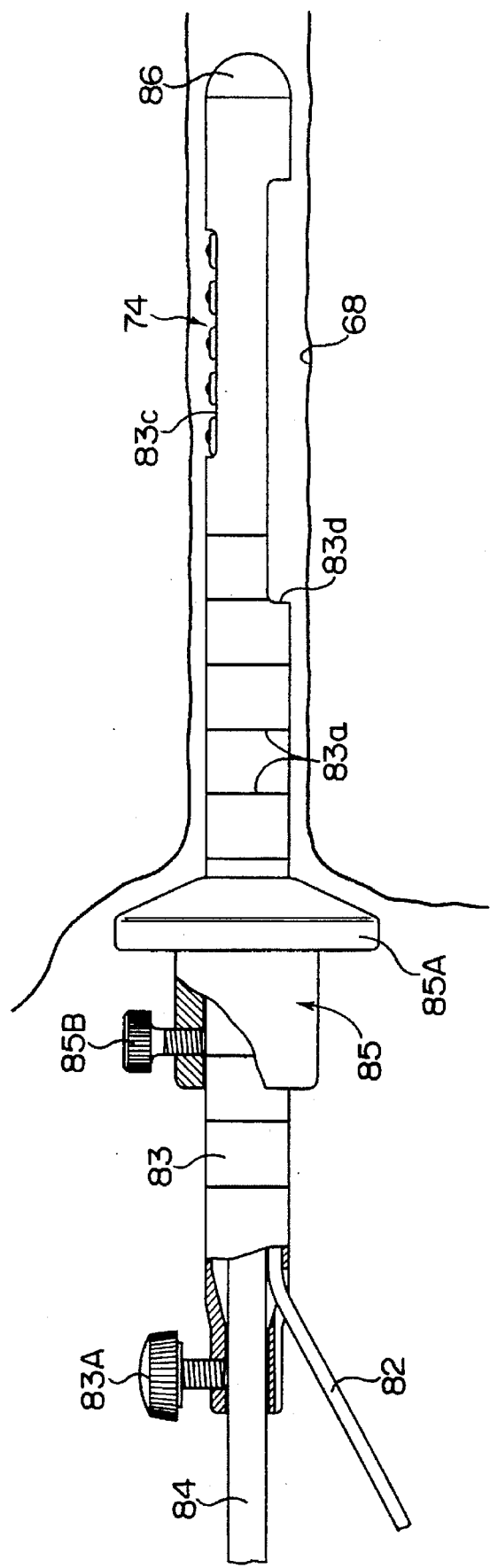
FIG. 10 is a front view of the catheter of FIG. 9.

After the sheath 83 is inserted into the rectum 68 and the insertion position is determined as shown in FIG. 10, the stopper 85 is fixed. Alternatively, after the stop 85 is fixed to a preliminarily determined marking 83a, the sheath 83 is inserted into the rectum 68. The stop 85 has a collar 85A and is loosely adapted to the sheath so that it is movable along the sheath 83. The stop is fixed to the sheath 83 by means of a fixing bolt 85B. The collar 85 can restrict insertion of the sheath 83 into the rectum 68 and can prevent insertion of the sheath due to an unwanted external force during operation.

The probe 84 may be inserted into the sheath 83 and positioning of the probe 84 on the sheath 83 is accomplished by the fixing bolt 83A passing through the sheath 83.

A reference 82 denotes a protection tube which surrounds the leads 74b for protection thereof and the leads are electrically connected with the temperature control unit 24 as is similar to the first embodiment.

Figure 11:
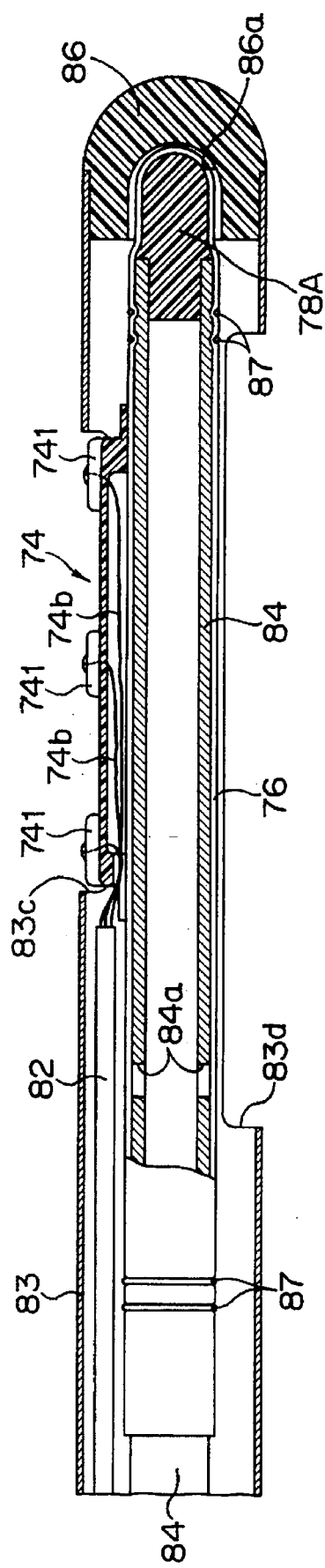
FIG. 11 is a longitudinal sectional view of the catheter of FIG. 9.

As shown in FIG. 10, the sheath 83 is closed at the front end thereof with a plug 86 made of plastics material. The plug 86 is the preferably hemispherical in outer shape to facilitate smooth insertion into the rectum 68. The plug 86 is formed on the outer surface with a hemispherical stop 86a (as shown in FIG. 11).

Figure 12:
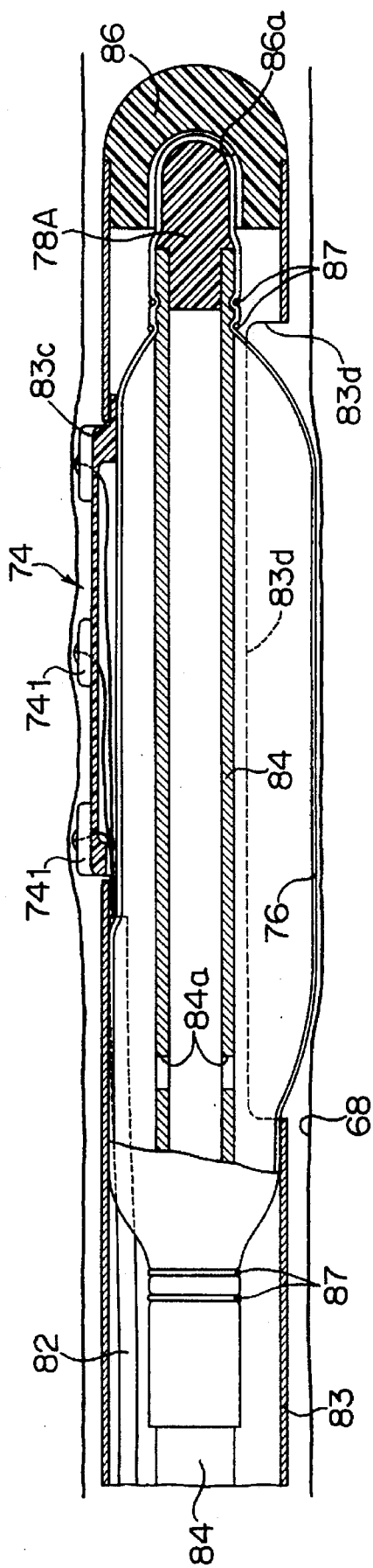
FIG. 12 is a longitudinal sectional view showing that the balloon is inflated.

The probe 84 is made of a stainless steel. A plug 78A of plastics is fitted to the front end thereof. The probe 84 is closed at the front end thereof and is hollow in shape. The probe 84 is provided with a balloon 76 having a bottom, made of rubber latex which surrounds the plug 78A. The balloon 76 is secured to the probe 84 with strings 87. The balloon 76 may be secured to the probe 84 with adhesive. The probe 84 is formed on the wall thereof with communicating holes 84a. If fluid such as air is supplied via the probe 84, a pneumatic pressure will be applied, upon the inner wall of the balloon 76 via the communicating holes 84 so that the balloon 78 will be inflated as shown in FIG. 12.

The sheath 83 is formed in the wall of the front end portion thereof with a substantially rectangular window 83c (refer to FIG. 9). The thermal sensor 74 is positioned within the window 83c. The thermal sensor 74 is provided on the outer surface of the balloon 76. On the other hand, the sheath 83 is provided with a window for inflating the balloon on the side opposite to the thermal sensor 74.

The thermal sensor 74 is somewhat complicated in shape. The shape will be understood from FIGS. 13 to 15. The thermal sensor 74 comprises a sensor holder made of plastic castings and thermocouples serving as sensor elements. The sensor holder has five protuberances 741 which are disposed in a zig-zag manner on the outer surface thereof (refer to FIG. 9) and has a recess 742 on the inner surface thereof and has two collar 743A and 743B at the front and rear sides, respectively. The rear collar 743B is formed with a notch 744 which is communicated with the recess 742 as shown in FIG. 14.

The leads 74b having thermocouples at the front ends pass through the wall of the above mentioned thermal sensor 74 and reach the surfaces of the protuberances 741 and are secured thereto with adhesive and the like. The leads 74b pass through the recess 742 and the notch 744 and are collected within the protection tube 82 and are connected to the temperature control unit 24.

In thus formed temperature detecting catheter apparatus 70, the sheath 80 is firstly inserted into the rectum 68 as shown in FIG. 10. When insertion is conducted, the thermal sensor 74 does not project as shown in FIGS. 11 and 13 and the outer surface thereof is substantially flush with the outer surface of the sheath 83. Therefore, the sheath 83 can be smoothly inserted into the rectum 68 without engagement of the thermal sensor 74 with the inner wall of the rectum 68.

Subsequently, air is compressed into the probe 84 and the air is introduced through communicating holes 84a for inflating the balloon 76 as shown in FIG. 12. In association with the inflation of the balloon 76, part of the balloon is inflated out from the inflation window 83d so that the sheath is biased upon the inner wall of the rectum 68. As a reaction, the thermal sensor 74 is pressed in a radial direction and is projected from the window 83c. As a result, the outer surface of each protuberance 741 is biased upon the inner wall. Therefore, accurate temperature of the inner wall of the rectum 68 is detected.

The temperature detection of the inner wall of the rectum 68 is conducted by means of the laser balloon catheter apparatus which is inserted into the urethra 60 at least during irradiation of the prostata 64 with laser light. A detected temperature signal is fed to the temperature control unit 24 as shown in FIG. 5 via each lead 74b from the inner wall of the rectum 68 as shown in FIG. 5. If the temperature exceeds a preset temperature at which the rectum 68 may be damaged, the power emitted from the laser light generator 26 is lowered or emission period is shorted.

After completion of the irradiation with the laser light, the laser balloon catherter apparatus is removed from the urethra 60 and the temperature detecting catheter apparatus 10 is also removed from the rectum 68. In case where the balloon 76 is deteriorated for a long period of use or by many repeated uses, the fixing bolt 83A is loosened and the probe 84 and the balloon 76 are removed from the sheath 83 and the existing balloon is replaced with new one. The probe 84 on which the new balloon is mounted is inserted into the sheath 83. Since the plug 78A portion is adapted into the engaging portion 86a of the plug 86 on insertion of the probe 84, the probe 84 is positively aligned with the center of the sheath 83.

Figure 16:
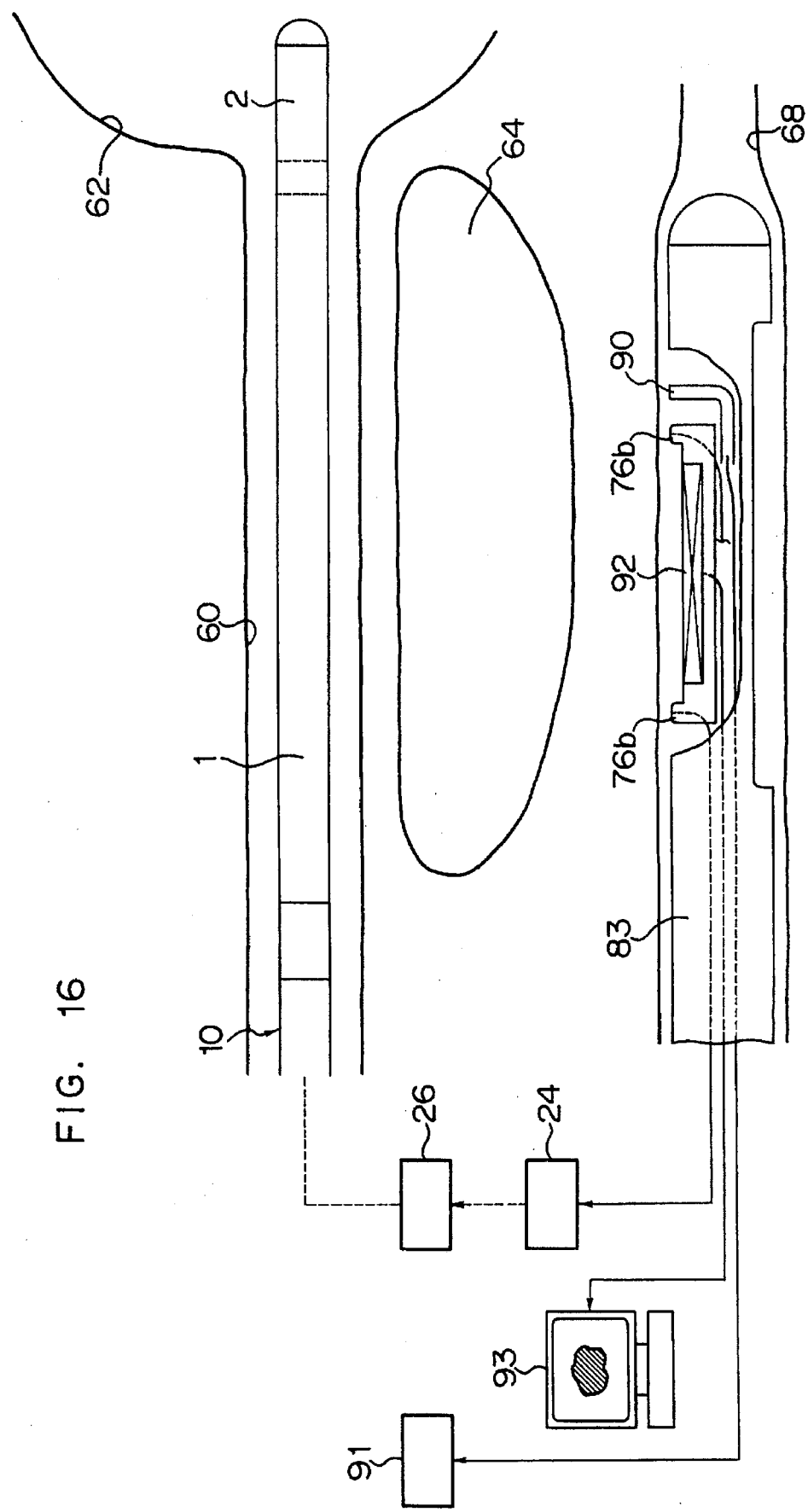
FIG. 16 is a schematic front view of a catheter apparatus having an alternative information detecting sensor.
Figure 17:
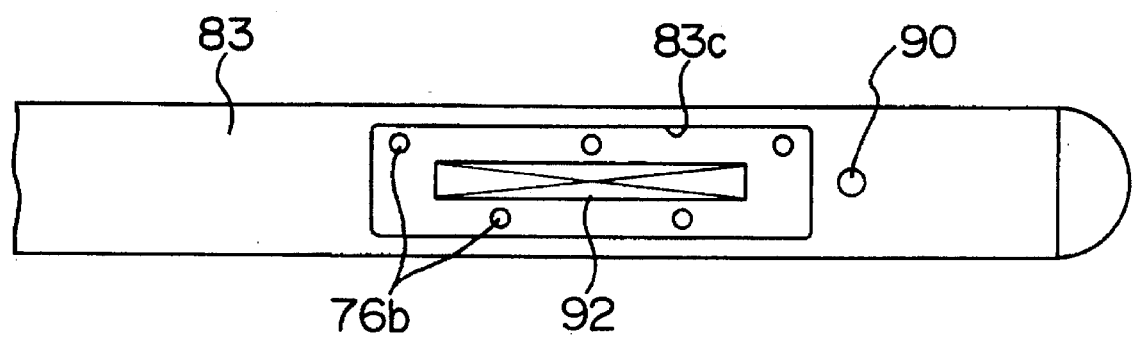
FIG. 17 is a plan view of the apparatus of FIG. 16.

In addition to temperature detection using the above-mentioned thermocouples as sensors in the information detecting catheter apparatus of the present invention, the leads 74b may be replaced with or separately added with optical fibers 90 as shown in FIGS. 16 and 17. The optical fibers 90 make it possible to detect laser light which reaches the inner wall of the rectum. The detected laser light is converted into an electrical signal representative of the received light quantity of the laser light by a photodiode 91 or a phototransistor. Since the quantity of the laser light has the correlation with the strength of the laser light which travels through the prostrate or is incident thereon, it may be used for controlling the amount of the laser light which is incident upon the prostata from the laser light generator. Since the amount of the received laser light has a correlation with the temperature of the prostata or the inner wall of the rectum, it can be used for controlling the laser light generator by converting into an electrical signal.

Since the amount of the received laser light is related with the insertion depth of the laser balloon catherter into the urethra, it may be used for adjusting the insertion position of the laser balloon catherter into the urethra depending thereon.

An ultrasonic diagnostic sensor may be used together with temperature detection using thermocouple or detection of the amount of laser light with the optical fiber 90. That is, an ultrasonic probe 92 is provided as shown in FIGS. 16 and 17. Ultrasonic waves are emitted toward the prostata 64 from the ultrasonic probe 92. The ultrasonic waves which are reflected by the prostata 64 are received. While tomographic image of the prostata is displayed on a CRT display 93, position of the prostata 64 and change in the prostata 64 in association with the projection of the laser light can be detected. It is preferable to determine the position of the prostata 64 with respect to the graduations 83a.

For conducting hyperthermia treatment of the prostata cancer, obtaining of the tomographic image of the prostata 64 using ultrasonic probe 92 is very effective.

The catheter apparatus of the present invention having a sensor for obtaining information may be used for obtaining desired object by inserting other body cavities such as esophagus and bronchia.

As mentioned above, the present invention offers advantages in that treatment effects in the position which is irradiated with laser light, such as degree of solidification and necrosis can be positively controlled in laser light irradiation treatment for the prostata and the like.

What is claimed is:

1. A catheter apparatus having a sensor, which is insertable into a body cavity for detecting information receivable at a wall of the body cavity or transmitted therethrough, comprising:

a rigid sheath which is to be inserted into said body cavity;

a first window provided on a side of a front end portion of the sheath to enable a sensor to move in or out therethrough, and a second window provided on a side opposite to said first window for a balloon to be inflated out therethrough;

a sensor positioned within said first window and movable in or out therethrough in a radial direction of said sheath; and a balloon means comprising a rigid probe and a balloon mounted thereon, the balloon being inflated or deflated by adjustment of a fluid pressure provided therein, whereby said balloon means is inserted into said sheath and said balloon during use is biased to the wall of said body cavity through said second window when said balloon is inflated, said sensor being thereby positively brought into close contact with the wall of said body cavity through said first window by a reaction force exerted on said sensor by said inflated balloon.

2. The catheter apparatus according to claim 1, wherein:

said sensor is adapted to detect at least one of a temperature of adjacent body tissue, a quantity of laser light and a level of ultrasonic energy transmitted to body tissue being treated.

3. The catheter apparatus according to claim 1, wherein:

the probe has a hollow body which is closed at a front end and is formed with a communicating hole in a wall of a front end portion, the balloon being formed and disposed so as to surround the communicating hole, the balloon being inflated by pressurized fluid supplied through the communicating hole via the inside of the hollow body.

4. The catheter apparatus according to claim 1, wherein:

the probe is longer than the sheath and is removably disposed within the sheath, the probe being secured to the sheath at a base end thereof.

5. The catheter apparatus according to claim 1, wherein:

the sheath is formed with an outer surface provided with graduations which are spaced apart in a longitudinal direction of the sheath for indicating a degree of insertion of the sheath into the body cavity.

6. The catheter apparatus according to claim 1, wherein:

the sheath is provided on an outer surface thereof with a stop shaped as a collar, said stop being movable in a longitudinal direction of the sheath and is provided with means for securing the stop to the sheath.

7. The catheter apparatus for detecting information as defined in claim 1, wherein:

the sensor comprises a sensor holder and sensor terminals, the sensor holder being provided on an outer surface with a plurality of protuberances, the sensor terminals being located on the protuberances.

* * * * *